(12) United States Patent
Minakami et al.

(10) Patent No.: US 9,823,190 B2
(45) Date of Patent: Nov. 21, 2017

(54) PARTICLE COUNTER FOR CHEMICAL SOLUTION

(71) Applicant: RION CO., LTD., Tokyo (JP)

(72) Inventors: Takashi Minakami, Tokyo (JP); Masaki Shimmura, Tokyo (JP); Tomonobu Matsuda, Tokyo (JP)

(73) Assignee: RION CO., LTD., Tokyo (JP)

( * ) Notice: Subject to any disclaimer, the term of this patent is extended or adjusted under 35 U.S.C. 154(b) by 25 days.

(21) Appl. No.: 14/859,780

(22) Filed: Sep. 21, 2015

(65) Prior Publication Data

US 2016/0091407 A1 Mar. 31, 2016

(30) Foreign Application Priority Data

Sep. 25, 2014 (JP) .................................. 2014-195877

(51) Int. Cl.
*G01N 15/14* (2006.01)
*G01N 21/53* (2006.01)
(Continued)

(52) U.S. Cl.
CPC ......... *G01N 21/53* (2013.01); *G01N 15/1459* (2013.01); *G01N 2015/0053* (2013.01);
(Continued)

(58) Field of Classification Search
CPC ................................................ G01N 15/1459
See application file for complete search history.

(56) References Cited

U.S. PATENT DOCUMENTS

2009/0153857 A1* 6/2009 Matsuda ............ G01N 15/0205
356/339
2012/0105967 A1* 5/2012 Hunter ............... G01N 15/1436
359/634
(Continued)

FOREIGN PATENT DOCUMENTS

JP         S62-293143 A     12/1987
JP         H02-075934 A      3/1990
(Continued)

OTHER PUBLICATIONS

Notice of Reason for Refusal for Japanese Patent Application No. 2014-195877 dated Nov. 27, 2014.

*Primary Examiner* — Shawn Decenzo
(74) *Attorney, Agent, or Firm* — Rankin, Hill & Clark LLP

(57) ABSTRACT

A particle counter for chemical solution in this disclosure uses a flow cell through which a chemical solution including particles flows, a laser light, and a light-receiving element array. Scattered light from the particles passing through a detection region on an optical path of the laser light in the flow cell is condensed to the light-receiving element array. The laser light in the center of the detection region has an energy density of $3 \times 10^8$ mW/cm$^2$ or more. Each of plural light-receiving elements (a) is larger in length and width than a spot diameter of the scattered light, and (b) receives the scattered light from a region with a size of 760 μm$^2$ or less included in the detection region. The signal processing unit counts the particles passing through the detection region by use of a threshold corresponding to the smallest measurable particle size of 0.03 μm.

2 Claims, 5 Drawing Sheets

(51) Int. Cl.
 *G01N 15/00* (2006.01)
 *G01N 21/03* (2006.01)
 *G01N 21/51* (2006.01)

(52) U.S. Cl.
 CPC ......... *G01N 2015/1486* (2013.01); *G01N 2021/0392* (2013.01); *G01N 2021/513* (2013.01)

(56) References Cited

U.S. PATENT DOCUMENTS

| | | | | |
|---|---|---|---|---|
| 2014/0152986 A1* | 6/2014 | Trainer | ............... | G01N 15/0205 356/336 |
| 2014/0200240 A1* | 7/2014 | Gabriel | ................. | G01N 33/49 514/301 |
| 2014/0234865 A1* | 8/2014 | Gabriel | ............. | G01N 33/5008 435/7.21 |
| 2014/0268079 A1* | 9/2014 | Kim | ...................... | G03F 7/7085 355/67 |
| 2015/0211977 A1* | 7/2015 | Sekimoto | ............... | G01N 15/10 356/338 |

FOREIGN PATENT DOCUMENTS

| | | | |
|---|---|---|---|
| JP | 11211651 A | * | 8/1999 |
| JP | 2011-013162 A | | 1/2011 |
| JP | 2011-059046 A | | 3/2011 |
| JP | 2012-251886 A | | 12/2012 |
| JP | 2014-092468 A | | 5/2014 |
| JP | 2014-092507 A | | 5/2014 |

\* cited by examiner

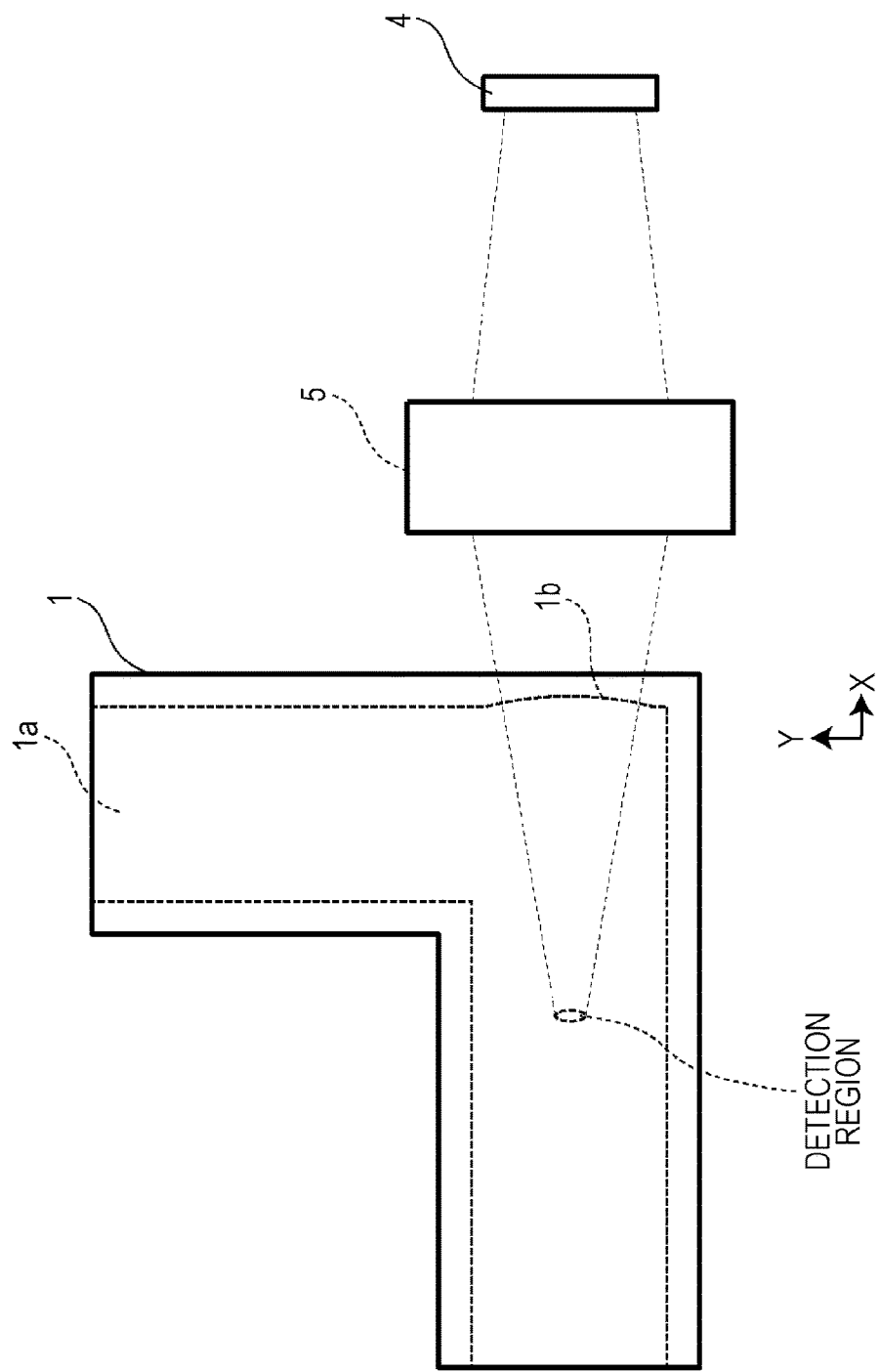

PARTICLE COUNTER FOR CHEMICAL SOLUTION

CROSS-REFERENCE TO RELATED APPLICATION

This application claims priority from Japanese Patent Application No. 2014-195877 filed with the Japan Patent Office on Sep. 25, 2014, the entire contents of which are hereby incorporated by reference.

BACKGROUND

1. Technical Field

This disclosure relates to a particle counter for chemical solution.

2. Related Art

In the manufacture of semiconductor wafers, the improvement of yields is an important issue. In this regard, impurity particles included in a chemical solution affect manufacturing processes. ITRS (International Technology Roadmap for Semiconductors) specifies the size of particles to be controlled in a chemical solution. Accordingly, it can be checked whether the chemical solution meets the standards by counting the particles in the chemical solution.

A particle counter is provided as a device for measuring particles in a chemical solution at relatively low cost. At the particle counter, the flowing chemical solution is irradiated with laser light. Then, scattered light from the particles in the irradiated flowing chemical solution is observed to count the particles.

However, the chemical solution also scatters laser light. Thus, in the case of measuring particles in a chemical solution, larger background noise occurs as compared to the case of measuring particles in the water. Accordingly, some particle counter is improved in the SN ratio by attenuating a high-frequency component resulting from background noise included in a detection signal (for example, see JP-A-2014-92507).

SUMMARY

A particle counter for chemical solution in this disclosure includes: a flow cell forming a flow passage for a chemical solution including particles; a light source for laser light; a light-receiving element array having a plurality of light-receiving elements; an irradiation optical system that irradiates the chemical solution with the laser light in a vertical direction against a direction in which the chemical solution flows through the flow passage; a condensing optical system that condenses, to the light-receiving element array, scattered light from the particles passing through a detection region on an optical path of the laser light in the flow passage; and a signal processing unit that counts the particles passing through the detection region based on an output signal from the light-receiving element array. The laser light in the center of the detection region has an energy density of $3 \times 10^8$ mW/cm² or more. Each of the plurality of light-receiving elements (a) is larger in length and width than a spot diameter of the scattered light from the particles, and (b) receives, via the condensing optical system, the scattered light from the particles passing through a region with a size of 760 μm² or less included in the detection region. The signal processing unit counts the particles passing through the detection region by use of a threshold corresponding to the smallest measurable particle size of 0.03 μm.

BRIEF DESCRIPTION OF DRAWINGS

FIG. 2 is a side view of the particle counter for chemical solution illustrated in FIG. 1;

DETAILED DESCRIPTION

Figure 1:
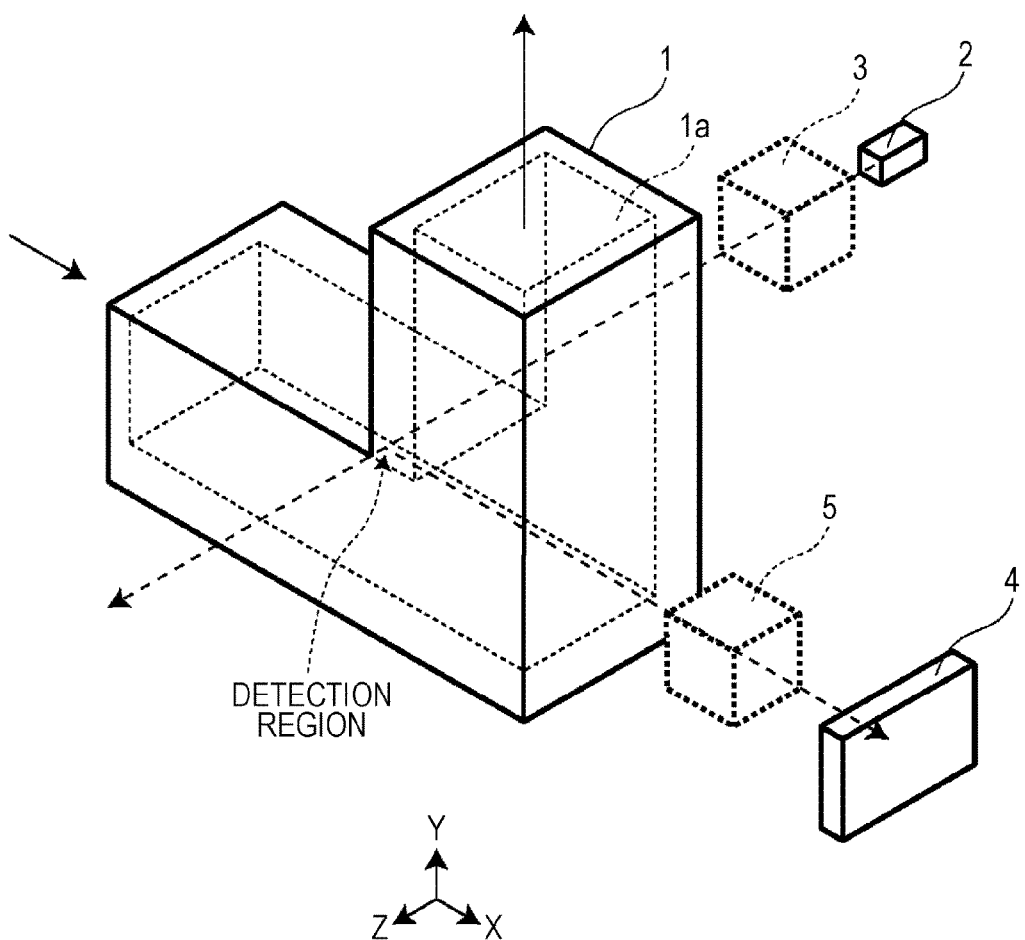
FIG. 1 is a perspective view illustrating an optical structure of a particle counter for chemical solution according to an embodiment of this disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In recent years, according to the refinement of manufacturing process based on technical progress in the manufacture of semiconductor wafers, wafers of ultra-fine structure with a half-pitch of 20 nm are materialized as mass production. Accordingly, there is demand for particle counters capable of counting particles with a size of 0.03 μm in a chemical solution. Particle counters capable of counting particles with a size of 0.04 μm in a chemical solution are currently on the market. However, it is difficult to count particles with a size of 0.03 μm in a chemical solution.

Figure 5:
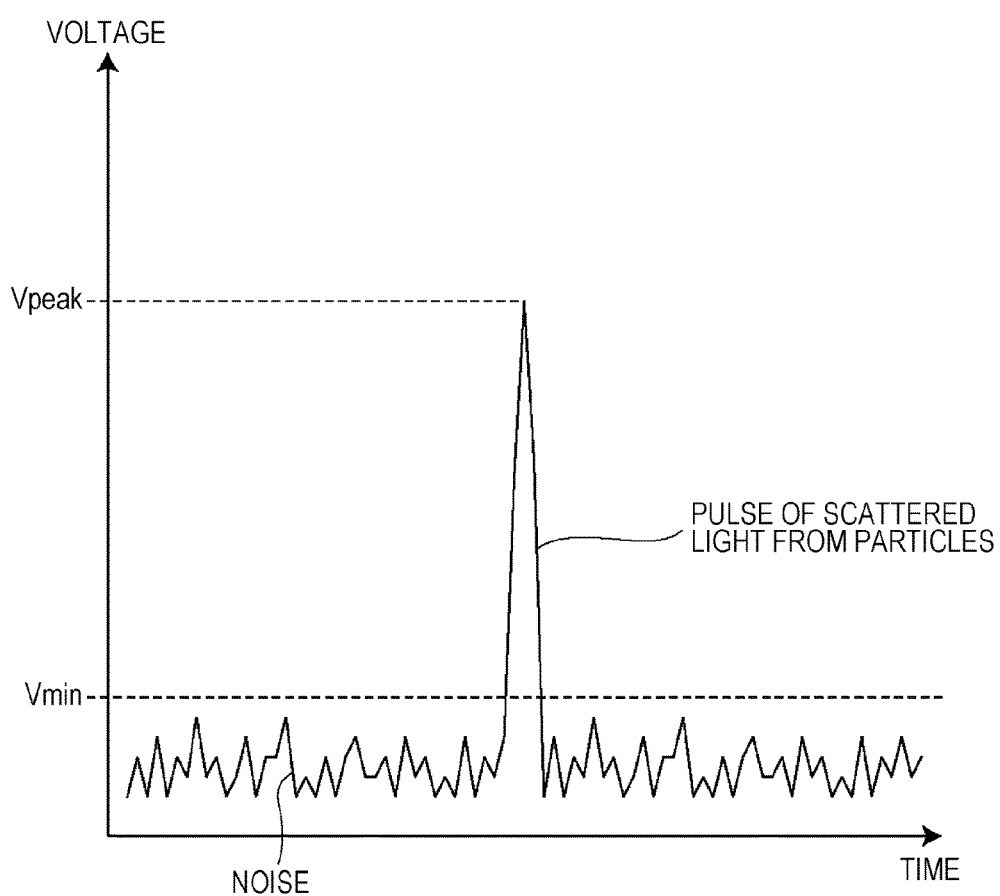
FIG. 5 is a chart for describing a detection signal of scattered light at the particle counter.

FIG. 5 is a chart for describing a detection signal of scattered light at the particle counter. As illustrated in FIG. 5, a voltage higher than a noise level is set as a threshold. Pulses detected when a pulse height value Vpeak of a detection signal resulting from scattered light from particles exceeds the threshold are counted.

Specifically, a threshold Vmin corresponding to the smallest measurable particle size is set such that the pulse height value corresponding to the smallest measurable particle size is higher than the noise level. Based on the threshold Vmin, the pulse of the scattered light from the particles needs to be differentiated from the noise. In general, when particles have a particle size sufficiently smaller than the wavelength of light emitted from a light source, the intensity of scattered light from the particles is proportional to the sixth power of the particle size (Rayleigh scattering). Accordingly, the pulse height value Vpeak is lowered as the particle size is smaller. Thus, a particle counter capable of counting particles with a size of 0.04 μm in a chemical solution does not have a capability, as it is, of counting particles with a size of 0.03 μm in a chemical solution.

A particle counter for chemical solution in this disclosure is devised in view of the foregoing problem. An object of this disclosure is to provide a particle counter for chemical solution that is capable of counting particles with a size of 0.03 μm in a chemical solution.

A particle counter for chemical solution according to an embodiment of this disclosure includes: a flow cell forming a flow passage for a chemical solution including particles; a light source for laser light; a light-receiving element array having a plurality of light-receiving elements; an irradiation optical system that irradiates the chemical solution with the laser light in a vertical direction against a direction in which the chemical solution flows through the flow passage; a condensing optical system that condenses, to the light-receiving element array, scattered light from the particles passing through a detection region on an optical path of the laser light in the flow passage; and a signal processing unit that counts the particles passing through the detection region based on an output signal from the light-receiving element array. The laser light in the center of the detection region has an energy density of $3\times10^8$ mW/cm$^2$ or more. Each of the plurality of light-receiving elements (a) is larger in length and width than a spot diameter of the scattered light from the particles, and (b) receives, via the condensing optical system, the scattered light from the particles passing through a region with a size of 760 μm$^2$ or less included in the detection region. The signal processing unit counts the particles passing through the detection region by use of a threshold corresponding to the smallest measurable particle size of 0.03 μm.

According to this disclosure, there is provided a particle counter for chemical solution capable of counting particles with a size of 0.03 μm in a chemical solution.

The embodiment of this disclosure will be described below with reference to the drawings.

FIG. 1 is a perspective view illustrating an optical structure of a particle counter for chemical solution according to the embodiment of this disclosure. FIG. 2 is a side view of the particle counter for chemical solution illustrated in FIG. 1.

Referring to FIG. 1, a flow cell 1 is bent in an L shape. A flow passage 1a for a chemical solution containing particles is formed in the flow cell 1. The flow passage 1a has a 1×1-mm cross section (parallel to the YZ plane) in a rectangular shape. In this embodiment, the flow cell 1 is made of sapphire. The chemical solution contains isopropyl alcohol, hydrofluoric acid solution, acetone, or the like. The refractive index of the chemical solution ranges from 1.26 to 1.43.

A light source 2 is a laser light source that emits laser light. In an irradiation optical system 3, the chemical solution is irradiated with laser light emitted from the light source 2 in a vertical direction (Z direction in FIG. 1) against a direction (X direction in FIG. 1) in which the chemical solution flows through the flow passage 1a. In the irradiation optical system 3, a lens group as described in JP-A-2003-270120, for example, is used to shape the laser light to increase its energy density.

In this embodiment, the wavelength of the laser light from the light source 2 is 532 nm. The wavelength of the laser light from the light source 2 may be 532 nm or less. In this wavelength region (Rayleigh scattering region), the intensity of scattered light is inversely proportional to the fourth power of the wavelength. Accordingly, even if the wavelength is 532 nm or more, increasing the power of the laser light compensates for the intensity decreased in inverse proportion to the fourth power of the wavelength, for example. Further, in this embodiment, the power of the laser light from the light source 2 is 800 mW. The power of the laser light from the light source 2 may be 800 mW or more. Further, in this embodiment, the energy density of the laser light in the center of a later-described detection region in the irradiation optical system 3 is approximately $3\times10^8$ mW/cm$^2$. The energy density of the laser light in the center of the detection region may be approximately $3\times10^8$ mW/cm$^2$ or more. Even if the power of the laser light is lower than 800 mW, it is possible to increase the energy density to $3\times10^8$ mW/cm$^2$ or more. In this case, however, the cross-sectional area of the irradiation region (parallel to the XY plane) is decreased and thus the efficiency of counting samples flowing in the flow cell with a 1×1-mm cross section becomes lower than 5%.

A light-receiving element array 4 has plural light-receiving elements arranged in the Z direction. A condensing optical system 5 condenses, onto the light-receiving element array 4, scattered light from particles passing through the detection region on the optical path of the laser light in the flow passage 1a. The condensing optical system 5 is a spherical condensing lens, for example. The condensing optical system 5 has an optical axis that passes through the center of the detection region and the center of the light-receiving element array 4 and is in parallel to the direction (X direction in FIG. 1) in which the chemical solution flows through the flow passage 1a. That is, the detection region refers to a region which is the crossing point, in the flow cell, between the laser light and the space where the scattered light is condensed on the light-receiving element array 4 through the condensing optical system 5.

As illustrated in FIG. 2, a spherical concave portion 1b is formed on the inner wall of the flow cell 1 positioned between the detection region and the condensing optical system 5 described above. This suppresses the refraction of the scattered light entering into the inner wall of the flow cell 1 from the detection region.

Figure 3A:
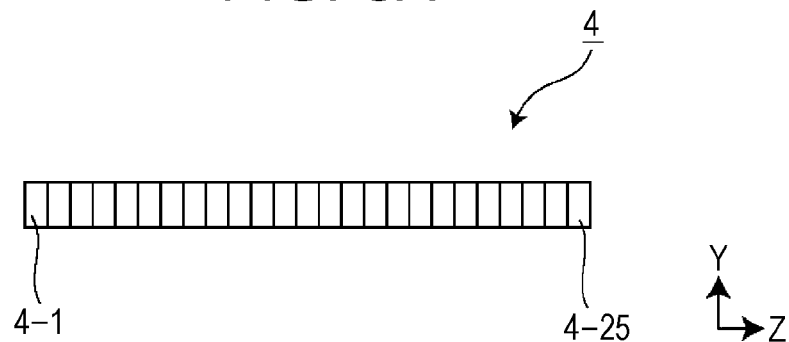
FIGS. 3A to 3C are diagrams for describing the relationship between a light-receiving element array 4 illustrated in FIG. 1 and a detection region corresponding to the light-receiving element array 4.
Figure 3B:
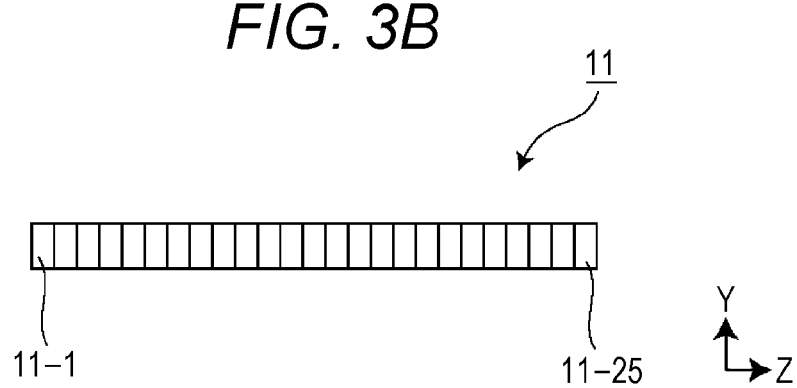
Figure 3C:
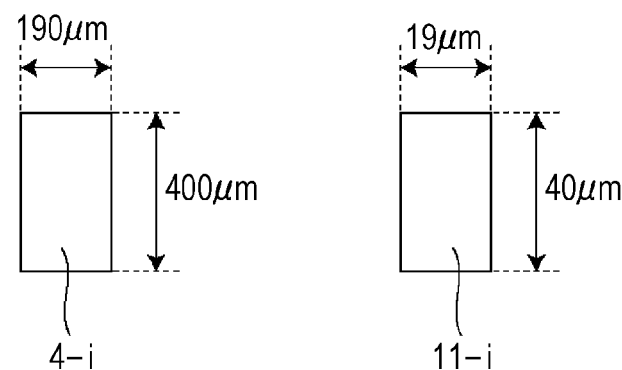
Figure 4:
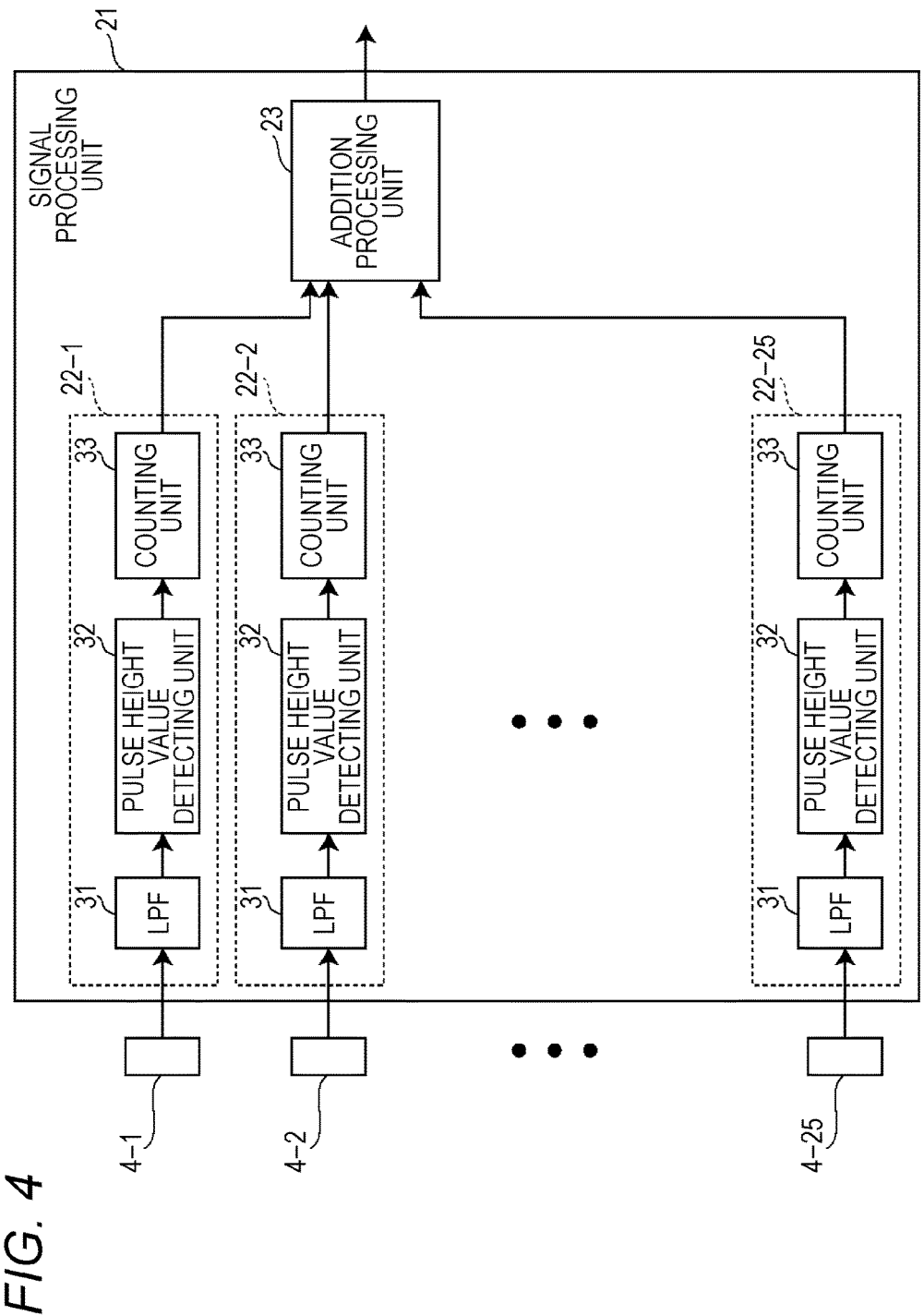
FIG. 4 is a block diagram illustrating an electrical structure of the particle counter for chemical solution according to the embodiment of this disclosure.

FIGS. 3A to 3C are diagrams for describing the relationship between the light-receiving element array 4 illustrated in FIG. 1 and the detection region corresponding to the light-receiving element array 4. FIG. 4 is a block diagram illustrating an electrical structure of the particle counter for chemical solution according to the embodiment of this disclosure.

In this embodiment, as illustrated in FIG. 3A, the light-receiving element array 4 includes 25 light-receiving elements 4-1 to 4-25. As illustrated in FIG. 3B, a detection region 11 corresponding to the light-receiving element array 4 is composed of regions 11-1 to 11-25 corresponding to the light-receiving elements 4-1 to 4-25, respectively. Using the light-receiving element array decreases the areas of the individual light-receiving elements. This can reduce the noise level resulting from the background light. In this embodiment, as illustrated in FIG. 3C, the size of the light-receiving element 4-$i$ is 190 μm (Z direction)×400 μm (Y direction), and the size of the region 11-$i$ is 19 μm (Z direction)×40 μm (Y direction). That is, the condensing optical system 5 is designed with a magnification of 10 times. In this embodiment, the size (area) of the region 11-$i$ corresponding to one light-receiving element 4-$i$ is 760 μm$^2$ (19 μm×40 μm). However, the size (area) may be smaller than that. In addition, the spot diameter of the scattered light on the light-receiving element in the vicinity of the center of the detection region is approximately 30 μm. The length and width of the light-receiving element 4-$i$ may be larger than this value (approximately 30 μm). In this embodiment, the size of the detection region 11 is 19,000 μm$^2$ (475 μm×40 μm). Accordingly, the counting efficiency is approximately 5% taking the flow velocity distribution into account.

Referring to FIG. 4, a signal processing unit 21 includes counting processing units 22-$i$ respectively corresponding to the light-receiving elements 4-$i$ (i=1, . . . , 25) and an addition processing unit 23 that calculates the sum of results from the counting processing units 22-1 to 22-25.

Each of the counting processing units 22-$i$ (i=1, . . . , 25) counts particles passing through each of the regions, which are corresponding to each of the light-receiving elements 4-$i$, included in the detection region based on output signals from each of the light-receiving elements 4-$i$. Each counting processing unit 22-$i$ includes a low-pass filter 31, a pulse height value detecting unit 32, and a counting unit 33. By the filter characteristics of the low-pass filter 31, a signal component with a higher frequency than the pulse resulting from the scattered light from the particles is attenuated. The pulse height value detecting unit 32 detects the pulse height values of pulses included in an output signal from the low-pass filter 31. The counting unit 33 detects the particles by comparing the pulse height value of each of the pulses detected by the pulse height value detecting unit 32 to the threshold corresponding to the particle size. When the particles are detected, the number of the particles is counted.

The counting units 33 included in the signal processing unit 21 can count the particles in the detection region by the use of a threshold corresponding to the smallest measurable particle size of 0.03 µm. The counting units 33 may count the particles with a size corresponding to each of plural particle size categories corresponding to plural thresholds.

Next, operations of the particle counter for chemical solution will be described.

A chemical solution is flown through the flow passage 1$a$ in the flow cell 1 so as to form a laminar flow at a flow rate of 10 mL/min. The laser light emitted from the light source 2 is shaped in the irradiation optical system 3. The chemical solution is irradiated with the shaped laser light. The scattered light from the particles passing through the regions 11-$i$ of the detection region 11 is condensed by the condensing optical system 5 onto any of the light-receiving elements 4-$i$ in the light-receiving element array 4.

When the scattered light from the particles is condensed to the light-receiving elements 4-$i$, the light-receiving elements 4-$i$ output pulses corresponding to the scattered light. Then, at the signal processing unit 21, the counting processing units 22-$i$ count the particles based on the pulses.

As described above, at the particle counter for chemical solution according to the embodiment, the wavelength of the laser light is 532 nm or less. The power of the laser light is 800 mW or more. The energy density of the laser light in the center of the detection region is $3 \times 10^8$ mW/cm$^2$ or more. The light-receiving element array 4 has the plural light-receiving elements. Each light-receiving element 4-$i$ receives, via the condensing optical system 5, the scattered light from the particles passing through the region of a size of 760 µm$^2$ or less included in the detection region 11. The signal processing unit 21 can count the particles passing through the detection region by the use of the threshold corresponding to the smallest measurable particle size of 0.03 µm.

Thus, the particles with a size of 0.03 µm in the chemical solution can be counted. It has been proven that particles with a size of 0.03 µm can be counted, by experiments in accordance with specifications for the size of each of the regions 11-$i$ included in the detection region 11, the condition for the laser light, and the threshold corresponding to the smallest measurable particle size of 0.03 µm.

The foregoing embodiment is a preferable example of this disclosure. However, this disclosure is not limited to the foregoing embodiment. The foregoing embodiment can be modified or changed in various manners without deviating from the technical scope of this disclosure.

This disclosure is applicable to counting of particles in a chemical solution for use in the manufacture of semiconductor wafers, for example.

The particle counter for chemical solution in this disclosure may be the following first or second particle counter for chemical solution.

The first particle counter for chemical solution includes: a flow cell forming a flow passage for a chemical solution; a light source for laser light; a light-receiving element array; an irradiation optical system that irradiates the chemical solution with the laser light in a vertical direction against a direction in which the chemical solution moves through the flow passage; a condensing optical system that condenses, to the light-receiving element array, scattered light from the particles in a detection region on an optical path of the laser light in the flow passage; and a signal processing unit that counts the particles in the detection region based on an output signal from the light-receiving element array, wherein the laser light in the center of the detection region has an energy density of $3 \times 10^8$ mW/cm$^2$ or more, the light-receiving element array has plural light-receiving elements, each of the plural light-receiving elements (a) is larger in length and width than a spot diameter of the scattered light from the particles, and (b) receives, via the condensing optical system, the scattered light from the particles in a region with a size of 760 µm$^2$ or less in the detection region, and the signal processing unit can count the particles in the detection region according to a threshold corresponding to the smallest measurable particle size of 0.03 µm.

In the second particle counter for chemical solution according to the first particle counter for chemical solution, the laser light has a wavelength of 532 nm, and the chemical solution has a refractive index in a range from 1.26 to 1.43.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A particle counter for chemical solution, comprising:
 a flow cell forming a flow passage for a chemical solution including particles;
 a light source for laser light;
 a light-receiving element array having a plurality of light-receiving elements;
 an irradiation optical system that irradiates the chemical solution with the laser light in a vertical direction against a direction in which the chemical solution flows through the flow passage;
 a condensing optical system that condenses, to the light-receiving element array, scattered light from the particles passing through a detection region on an optical path of the laser light in the flow passage; and
 a signal processing unit that counts the particles passing through the detection region based on an output signal from the light-receiving element array, wherein
 the particle counter is capable of counting the particles with a size of 0.03 µm in the chemical solution,
 the laser light in the center of the detection region has an energy density of $3 \times 10^8$ mW/cm$^2$ or more as long as the particle counter is capable of counting the particles with the size of 0.03 µm in the chemical solution, each of the plurality of light-receiving elements
- (a) is larger in length and width than a spot diameter of the scattered light from the particles, and
- (b) receives, via the condensing optical system, the scattered light from the particles passing through a region with a size of 760 μm$^2$ or less as long as the particle counter is capable of counting the particles with the size of 0.03 μm in the chemical solution, the region being included in the detection region, and the signal processing unit counts the particles passing through the detection region by use of a threshold corresponding to the smallest measurable particle size of 0.03 μm.

2. The particle counter for chemical solution according to claim 1, wherein the laser light has a wavelength of 532 nm, and
the chemical solution has a refractive index ranging from 1.26 to 1.43.

\* \* \* \* \*